United States Patent [19]

Cielo

[11] Patent Number: 4,490,618
[45] Date of Patent: Dec. 25, 1984

[54] OPTICAL SYSTEM FOR ANALYZING THE SURFACE OF A FIBROUS WEB

[75] Inventor: Paolo G. Cielo, Montreal, Canada

[73] Assignee: Canadian Patents & Development Limited, Ottawa, Canada

[21] Appl. No.: 367,686

[22] Filed: Apr. 12, 1982

[51] Int. Cl.³ .......................................... G01N 21/86
[52] U.S. Cl. ..................... 250/571; 356/429
[58] Field of Search ............. 250/571, 572, 562, 563, 250/227; 356/71, 238, 430, 431; 350/96.28

[56] References Cited

U.S. PATENT DOCUMENTS

| | | | |
|---|---|---|---|
| 3,565,565 | 2/1971 | Reid | 356/71 |
| 3,716,301 | 2/1973 | Caulfield et al. | 356/71 |
| 3,783,296 | 1/1974 | Blevins | 250/550 |
| 3,944,978 | 3/1976 | Jensen et al. | 356/71 |
| 4,019,066 | 4/1977 | Lucas et al. | 250/562 |
| 4,194,840 | 3/1980 | Lucas et al. | 356/429 |
| 4,213,708 | 7/1980 | Lucas | 356/429 |
| 4,411,490 | 10/1983 | Daniel | 350/96.28 |
| 4,414,684 | 11/1983 | Blonder | 356/71 |

OTHER PUBLICATIONS

"SELFOC" Single Microlens (SML), Nippon Sheet Glass Co., Ltd., Tokyo, Japan, 9/1/79.
Optics and Laser Technology, 6/1983, "Optical Inspection by Internal Reflection and Spatial Filtering", P. Cielo, pp. 145-149.

*Primary Examiner*—Davis L. Willis
*Assistant Examiner*—J. Brophy
*Attorney, Agent, or Firm*—Edward Rymek

[57] ABSTRACT

The apparatus for analyzing the surface of a fibrous web, such as a paper or a textile, includes a prism structure in which one surface is placed in contact with the fibrous web under a predetermined pressure. A collimated beam of light is directed into the prism on the contact surface. The light reflected from the contact surface through the prism is directed to a detector. The detector senses the light reflected by the contact surface as well as the light diffracted at the contact surface to indicate the surface condition of the fibrous web.

10 Claims, 8 Drawing Figures

OPTICAL SYSTEM FOR ANALYZING THE SURFACE OF A FIBROUS WEB

BACKGROUND OF THE INVENTION

This invention is directed to the measurement of the quality of a web, such as paper or textiles, and in particular, to an optical apparatus for analysing the surface of a fibrous paper or textile web.

The quality control of paper characteristics, such as strength and printability, is of prime concern to pulp and paper manufacturers. Important parameters in determining these characteristics are the dimensions of the fibers in the paper, their elasticity and their compactness. The coarseness or roughness of a paper or textile surface may be controlled in manufacture. Many methods of measuring quality which have been devised to date, do so in a non-real time situation, in that samples of the web are taken and analysed in a laboratory situation under microscope or the like. These measurements cannot be used to continuously control a process.

One method of measuring the graininess or roughness of a surface is described in U.S. Pat. No. 4,213,708, which issued on July 22, 1980; U.S. Pat. No. 4,194,840, which issued on Mar. 25, 1980; and U.S. Pat. No. 4,019,066, which issued on Apr. 17, 1977. This method consists of projecting a light spot on the surface of the web as it travels rapidly under the sensor. The light reflected by the web is detected in a single detector, the time-modulation component of the output signal from the detector is related to the graininess or roughness of the web. This method's accuracy is related to web speed and is not sensitive to small discontinuities.

A method for detecting deviations in a repetitive mesh pattern in a fabric is described in U.s. Pat. No. 3,783,296, which issued on Jan. 1, 1974. A collimated light beam is passed through the web to produce a diffracted pattern that is compared to a mesh pattern to detect any unacceptable deviation. This method requires transmission through a web having a repetitive pattern.

SUMMARY OF THE INVENTION

It is therefore an object of this invention to provide apparatus for optically analysing the surface of a fibrous web.

It is a further object of this invention for analysing the surface of a fibrous web accurately whether or not it is in motion.

These and other objects are achieved in an apparatus which includes a prism structure in which one surface is placed in contact with the fibrous web under a predetermined pressure. A collimated beam of light is directed into the prism onto the contact surface. The light reflected from the contact surface through the prism is directed to a detector. The detector senses the light reflected by the contact surface as well as the light diffracted at the contact surface to indicate the surface condition of the fibrous web.

In one embodiment of the invention, the prism may be oriented such that the light beam is transmitted into and out of the prism through the back surface of the prism while one of the refractive surfaces makes contact with the web. A pair of converging lenses which are made from glass cylinders having radial refractive index gradients, are mounted on the prism back surface to direct the light beam into and out of the prism. The light beam may be generated by light-emitting diode on the end of the lens or transmitted to the lens by an optical fiber. The detector may be made of two or more concentric photosensitive elements fixed to the end of the lens in order to sense the reflected beam as well as the diffracted light, or the detector may include a bundle of fibers to transmit the light from the lens to the sensors.

In accordance with another embodiment of the invention, the prism may be a toroidal prism mounted to rotate about an axis with a predetermined segment of its circumferential surface in contact with the fibrous web at any time.

A roller may be mounted opposite the contact surface of the prism to maintain the web in pressure contact with the web which may be a fibrous paper or textile.

Many other objects and aspects of the invention will be clear from the detailed description of the drawings.

DETAILED DESCRIPTION

Figure 1:
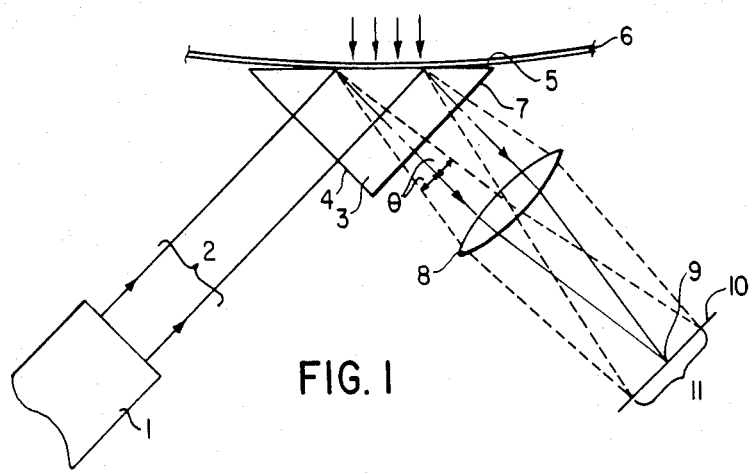
FIG. 1 schematically illustrates the surface analyser in accordance with the present invention.

The basis of the present invention is illustrated in FIG. 1 wherein a collimated light beam 2 from a source 1 is projected into a right angle prism 3 through one refracting surface 4 onto the back surface 5 of the prism 3. When a web 6 is not in contact with the back surface, the beam 2 is totally reflected from the back surface 5-air interface out of the prism 3 through its other refracting surface 7. This assumes that the angle of incidence of the light beam at the prism's contact surface 5 is larger than the critical angle for total internal reflection of the glass air interface, i.e. an angle of incidence of 45° or greater would be appropriate for a glass prism having a refractive index of 1.5. The beam 2 emerging from the prism 3 is focussed by a lens 8 to a point 9 on a screen or detector 10.

Figure 2:
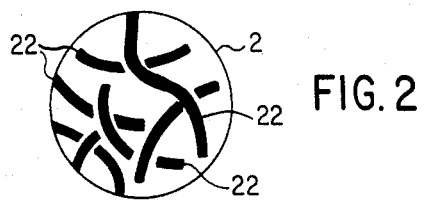
FIG. 2 illustrates a cross-section of the beam reflected from the prism contact surface.

When a fibrous web 6 is pressed against the back surface 5 of the prism 3, optical energy from the beam will be transmitted from the prism 3 to the web at all points where the fibers in the web 6 are in contact with the prism 3. From all other points, i.e. between the fibers, the beam 2 will be totally reflected and focussed onto point 9 of detector 10. It is understood that contact between the fibers and the prism 3 is defined as being a distance of 1 μm or less between the two. The cross-section of the reflected light beam 2 is represented in FIG. 2 wherein the fibers in a web 6, such as paper, appear as dark areas 22 whose dimensions are related to the dimensions of the fibers.

Since the beam is amplitude modulated across its cross-section, diffractions will occur which, as represented in FIG. 1, will cause an enlargement of the beam about the focus point 9 at the detector 10. In addition, the angles $\theta$ of diffraction of the light will vary inversely with the width of the shadow areas 22, i.e. the narrower the shadow areas, the larger the diffraction angles $\theta$ and, therefore, the larger the illuminated area 11 on the detector 10. This relationship is based on the Fourier transform from which it is known that the distribution of the beam intensity about focus point 9 is a function of the spatial distribution of the frequencies of the incident beam.

The average diameter of the fibers in the web can, therefore, be determined from the size of the diffracted light image 11 on the detector 10. In addition, the ratio between the intensity of the diffracted light and the intensity of the light detected at point A determines the surface area of the prism contacted by fibers in the web at a preselected pressure. This is a measure of web graininess or roughness. This method is particularly applicable to surface having a graininess in the order of 10 to 200 $\mu$m.

Figure 3:
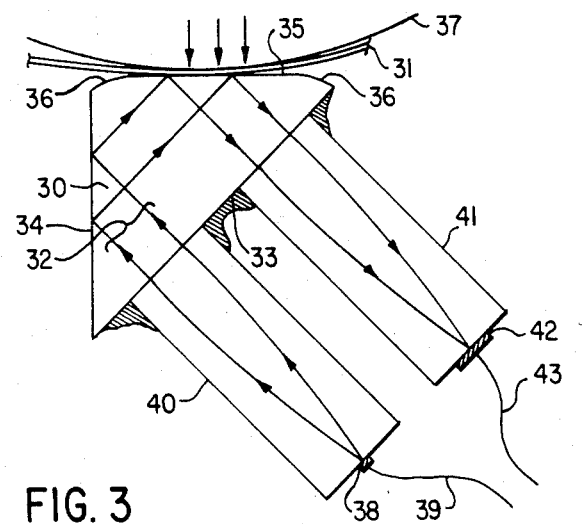
FIG. 3 illustrates an embodiment of the analyser using a stationary prism.

One embodiment of the apparatus in accordance with the present invention is illustrated in FIG. 3. A right angle prism 30 is used as the sensor which makes contact with the web 31 to be analysed. In this embodiment however, the beam 32 is made to enter the prism 30 through the back surface 33, totally reflect off one refractive surface 35 which contacts the web 31, to exit from the prism 30 through the back surface. The refractive surface 35 may have rounded corners 36 to allow the web 31 to slide over surface 35 without snagging. The web 31 is pressed against the surface 35 by a roller 37 at a pressure in the order of 10N/mm$^2$.

The optics for the apparatus may include a photo-emitting diode 38, such as an RCA model C30199 diode, with its lead 39 fixed to a graded-index lens 40, the refractive index being greatest at the central axis of the lens and decreasing along its radius towards its perimeter. The lens 40 acts as a converging lens and causes the beam 32 emitted by diode 38 to become collimated as it is transmitted through the length of the lens 40. Graded index lenses, such as the Selfoc [trademark] lens marketed by Nippon Sheet Glass Ltd., are made from a number of coaxial glass cylinders that are drawn to reduce their diameters. Typical lenses would be in the order of 0.5 cm long and 2 mm in diameter. A further similar lens 41 receives the beam 32 from the prism 30 and focusses it onto a photodetector 42 with its leads 43, which is fixed to the end of lens 41. Lenses 40 and 41 are cemented to the prism 30 by an adhesive, such as epoxy, in order to obtain a minimum of reflections at the interfaces between the lenses 40, 41 and the prism 30. Since the lenses 40, 41, the photoemitter diode 38 and the photodetector 42 are all solidly fixed together, the optical system is compact and capable of operating in hostile mechanical environments with little risk of becoming misaligned.

Figure 4:
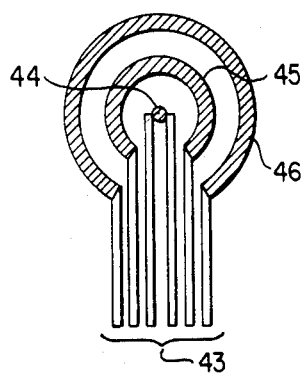
FIG. 4 illustrates a detector used in the analyser.

Photodetector 43 may take any of a number of forms which are capable of measuring the non-diffracted light focussed at a point on the axis of the lens 41 and the diffracted light which is peripheral to this focus point. One such embodiment is illustrated in FIG. 4. It consists of three concentric elements 44, 45 and 46 of photosensitive material, such as PbS, deposited directly onto the end of the lens 41 with the smallest photosensitive element 44 on the axis of the lens. Metal leads 43, also deposited on the end of lens 41, are connected to the three elements 44, 45 and 46. The photodetector 43 may alternately be a detector, such as the WRD 6400 available from Recognition Systems, Inc. or the IPI 31 available from IPI/Centronic.

Figure 5:
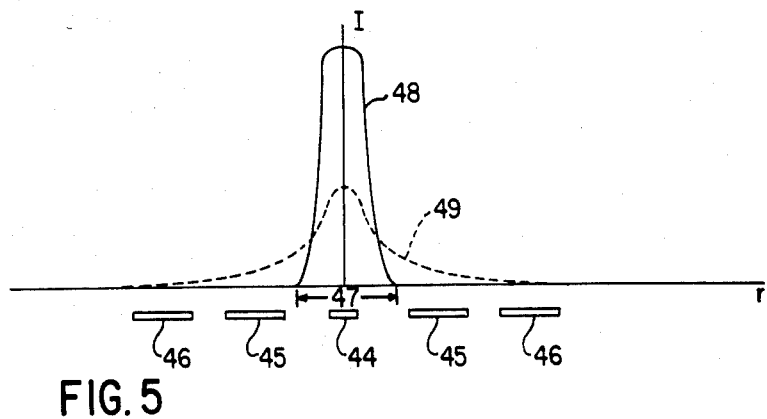
FIG. 5 illustrates the beam intensity across its cross-section at the detector.

Typical light intensity distribution curves across the diameter of a detector 43 are shown in FIG. 5. When a web is not pressed against the prism surface and the beam is totally reflected, the beam will be focussed to a small area 47 about the photosensitive element 44 shown by curve 48 in FIG. 4. The size of the area 47 will depend on the quality of the optics used in the system. For example, if the diode 38 emits a beam 32 having a diameter of 50 $\mu$m, and the lenses have a resolution of 50 lines/mm, the area 47 diameter will be approximately 70 $\mu$m. When a web is pressed against the prism 30 surface 35, the intensity curve will widen as represented by curve 49, and the intensity detected by sensor 44 will decrease. The ratio between the signals from sensors 45 and 44 determines the surface contact by the fibers in the web at a predetermined pressure and, therefore, the roughness of the surface, and the ratio between the signals from sensors 46 and 45 determines the average diameter of the fibers in the web, however, this reading is independent of the pressure applied to the web.

Figure 6:
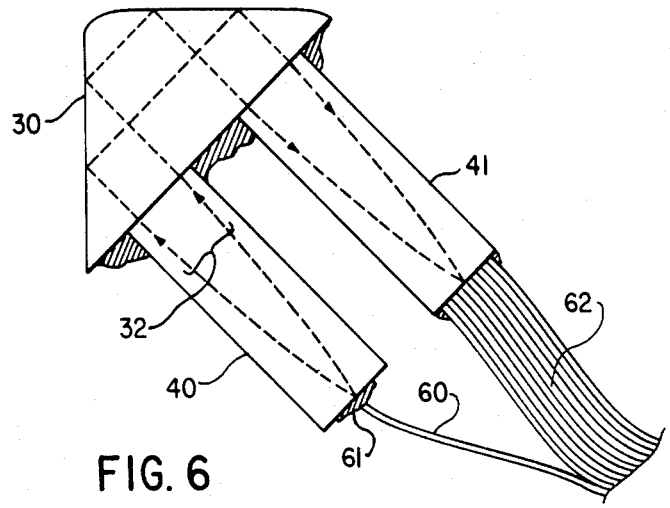
FIG. 6 illustrates a variation of the embodiment shown in FIG. 3.

An alternate detector to the version of the detector described in conjunction with FIG. 3 is shown in FIG. 6. The photo-emitting diode 38 is replaced by an optical fiber 60 cemented to lens 40 at its axis using an epoxy 61. The prism 30 is fixed to lenses 40 and 41 as in FIG. 3, however, detector 42 is replaced by a bundle of optical fibers 62 cemented to the end of lens 41. The fiber 60 feeds a beam 32 to the lens 40 and the bundle 62 receives the reflected and refracted beam from the lens 41. The optical fiber 60 must have a numerical aperture smaller than the aperture of the lens 40 in order to avoid spurious reflections at the lens walls. The fibers 62 are not subject to this restriction since they receive the light. Fiber 60 can, for example, be a Corning Glass model Corguide with a numerical aperture of 0.2, while fibers 62 could be Poly-Optical Products Inc. plastic fibers. The outputs from concentric groups of fibers in the bundle 62 may be fed to optical detectors to provide the output signals as in the device in FIG. 3, however these outputs may also be detected as radial segments which will provide information as to any predominant diffraction direction exhibited by the fibrous web. For example, parallel-aligned fibers would produce diffractions in directions perpendicular to the direction of the fibers.

Figure 7:
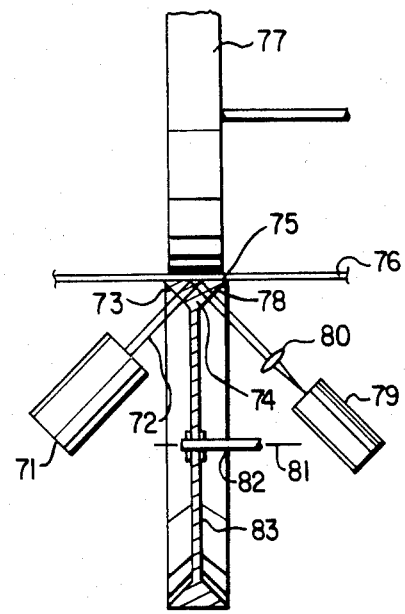
FIGS. 7 and 8 illustrate a further embodiment of the surface analyser in accordance with the present invention.
Figure 8:
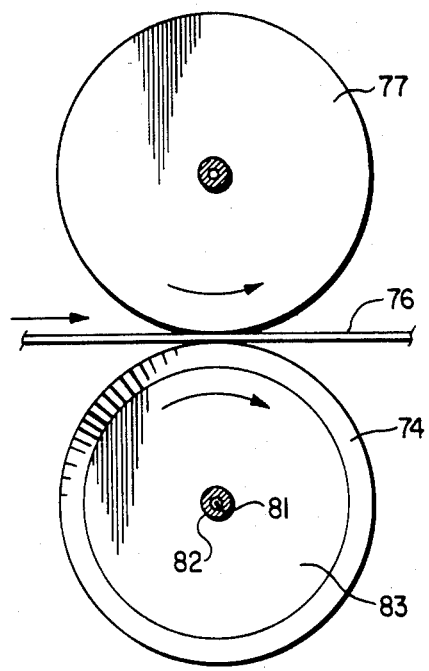

A further embodiment of a detector in accordance with the present invention is illustrated in FIG. 7. The operation of this embodiment is similar to the one shown in FIG. 1. A source 71 directs a collimated beam 72 onto one refractive surface 73 of right angle prism 74. The beam 72 is reflected from the back surface 75 which is in contact with a fibrous web 76. A roller 77 applies the desired pressure to the web 76. The beam 72 is transmitted from the prism 74 through the other refractive surface 78 and focussed onto a detector 79 by a lens 80. In this particular embodiment, however, elongated prism in the previous embodiments is replaced by a toroidal prism 74 with the circumferential surface forming the back surface and with the surfaces facing the axis 81 of the toroid forming the refractive surface. The prism 74 is fixed to an axle 82 by a wall 83 made of glass or other material so as to rotate about the axis 81. Pressure roller 77 and prism 74, therefore, rotate in opposite directions as the web 76 moves between them.

For proper operation of the analyser in accordance with the present invention, it is necessary that the spreading of the beam due to diffraction be greater than the diameter D of the beam itself. A slot or a groove having a width d will produce at the focal plane of a lens, a diffraction displacement 2r in the order of:

$$2r \approx 2f\theta = 2f\lambda/d \qquad (1)$$

where $\theta$ is the diffraction angle
f is the focal distance of the lens, and
$\lambda$ is the wavelength of the light.
Therefore, $$D < 2f\lambda/d, \text{ or } d < 2f\lambda/D \qquad (2)$$

For a detector in which $\lambda = 0.9$ μm, f = 1 cm and D = 70 μm, d will have to be smaller than 260 μm. In addition, in order not to lose the diffracted beam, the angle of diffraction will have to be smaller than the numerical aperture of the lens, i.e. in the order of 0.4 and, therefore, $$d > \lambda/\theta = 2.25 \text{ μm}$$

For ordinary newsprints which have fibers with diameters in the range of 10 to 100 μm, the above device wherein 2.25 μm < d < 260 μm will provide satisfactory results.

Many modifications in the above described embodiments of the invention can be carried out without departing from the scope thereof and, therefore, the scope of the present invention is intended to be limited only by the appended claims.

I claim:

1. Apparatus for analysing the surface of a fibrous web comprising:
    a prism having first and second refractive surface and a back surface, one refractive surface being adapted to be in contact with the fibrous web under a predetermined pressure;
    a light source means;
    a first radially graded-index lens with one end fixed to the back surface of the prism for collimating a light beam from the light source means and directing the collimated beam into the prism onto the contact surface;
    a detector means;
    a second graded-index lens with one end fixed to the back surface of the prism for focussing light received from the contact surface through the prism and directing the light onto the detector means, whereby the detector means senses light reflected by the contact surface and light diffracted at the contact surface to indicate the surface condition of the fibrous web.

2. Apparatus as claimed in claim 1 wherein the light source means is a photo-emitting diode fixed to the second end of the radially graded-index lens.

3. Apparatus as claimed in claim 1 wherein the light source means is an optical fiber for transmitting light to the radially graded-index lens.

4. Apparatus as claimed in claim 1 wherein the detector means is fixed to the second end of the second radially graded-index lens.

5. Apparatus as claimed in claim 4 wherein the detector means includes at least two concentric photosensitive elements fixed to the second end of the second radially graded-index lens to detect reflected light and to detect refracted light.

6. Apparatus as claimed in claim 5 wherein the detector means includes three concentric photosensitive elements.

7. Apparatus as claimed in claim 4 wherein the detector means includes a bundle of optical fibers optically coupled to the second end of the second radially graded-index lens.

8. Apparatus as claimed in claim 1 which further includes roller means for applying the fibrous web against back surface of the prism.

9. Apparatus as claimed in claim 1 which further includes roller means for applying the fibrous web against the prism means.

10. Apparatus for analysing the surface of a fibrous web comprising:
    a toroidal prism mounted to rotate about an axis with a predetermined segment of the circumferential surface of the toroid being adapted to be in contact with the fibrous web under a predetermined pressure at any time;
    first means for directing a collimated light beam into the prism onto the contact surface;
    second means for directing light reflected from the contact surface through the prism onto a detector means; and
    the detector means sensing the light reflected by the contact surface and the light diffracted at the contact surface to indicate the surface condition of the fibrous web.

* * * * *